US010010076B2

(12) United States Patent
Ratajczyk et al.

(10) Patent No.: US 10,010,076 B2
(45) Date of Patent: Jul. 3, 2018

(54) PLANT CONTROL COMPOSITION CONTAINING PEPTIDE ENHANCING AGENT

(71) Applicant: Arch Chemicals, Inc., Atlanta, GA (US)

(72) Inventors: William Alexander Ratajczyk, Reedsburg, WI (US); Ryan M. Wersal, Cumming, GA (US); John Weber, Liburn, GA (US)

(73) Assignee: Arch Chemicals, Inc., Atlanta, GA (US)

( * ) Notice: Subject to any disclaimer, the term of this patent is extended or adjusted under 35 U.S.C. 154(b) by 0 days.

(21) Appl. No.: 14/459,830

(22) Filed: Aug. 14, 2014

(65) Prior Publication Data

US 2015/0105257 A1    Apr. 16, 2015

Related U.S. Application Data

(60) Provisional application No. 61/865,679, filed on Aug. 14, 2013.

(51) Int. Cl.
| | | |
|---|---|---|
| *A01N 29/00* | (2006.01) | |
| *A01N 25/30* | (2006.01) | |
| *A01N 37/10* | (2006.01) | |
| *A01N 43/34* | (2006.01) | |
| *A01N 43/48* | (2006.01) | |
| *A01N 43/72* | (2006.01) | |
| *A01N 43/84* | (2006.01) | |
| *A01N 43/90* | (2006.01) | |
| *A01N 59/00* | (2006.01) | |
| *A01N 59/20* | (2006.01) | |
| *A01N 37/46* | (2006.01) | |
| *A01N 63/04* | (2006.01) | |

(52) U.S. Cl.
CPC ............. *A01N 37/46* (2013.01); *A01N 25/30* (2013.01); *A01N 37/10* (2013.01); *A01N 59/00* (2013.01); *A01N 63/04* (2013.01)

(58) Field of Classification Search
None
See application file for complete search history.

(56) References Cited

U.S. PATENT DOCUMENTS

| | | | |
|---|---|---|---|
| 5,747,416 A * | 5/1998 | McArdle | ........................ 504/115 |
| 7,476,529 B2 | 1/2009 | Podella et al. | |
| 8,323,949 B2 | 12/2012 | Podella | |
| 8,871,682 B2 | 10/2014 | Podella et al. | |
| 2010/0069245 A1 | 3/2010 | Scholer et al. | |
| 2010/0099599 A1 * | 4/2010 | Michalow et al. | ........... 510/375 |
| 2011/0190132 A1 * | 8/2011 | Petta | ..................... A01N 43/90 |
| | | | 504/136 |
| 2011/0319341 A1 * | 12/2011 | Awada | .................. A01N 25/30 |
| | | | 514/20.9 |
| 2012/0142530 A1 | 6/2012 | Michalow et al. | |
| 2014/0248373 A1 | 9/2014 | Michalow et al. | |

FOREIGN PATENT DOCUMENTS

| | | |
|---|---|---|
| EP | 0517378 | 12/1992 |
| EP | 0702897 | 3/1996 |
| WO | WO 01/60160 | 8/2001 |

OTHER PUBLICATIONS

Wisconsin Department of Natural Resources, "Chemical Fact Sheet: Simazine," published May 1990, pp. 1-4.*
BD Bionutrients™ Technical Manual, "Advanced Bioprocessing," Third Edition Revised, published Oct. 2006, pp. 1-68.*
Wisconsin Department of Natural Resources, "Fluridone Chemical Fact Sheet," published Jan. 2012, p. 1-2.*
Department of Ecology, "Aquatic Plant Management—Aquatic Herbicides," State of Washington, http://www.ecy.wa.gov/programs/wq/plants/management/aqua028.html, pp. 1-8.*
H. G. Peterson et al., "Aquatic phyto-toxicity of 23 pesticides applied at Expected Environmental Concentrations," Aquatic Toxicoloty 28 (1994) 275-292.*
International Search Report and Written Opinion for PCT/US2014/051032 dated Nov. 5, 2014.

* cited by examiner

*Primary Examiner* — Tracy Vivlemore
*Assistant Examiner* — Monica A Shin
(74) *Attorney, Agent, or Firm* — Dority & Manning, P.A.

(57) ABSTRACT

A plant or algae control composition is disclosed. The composition contains a herbicide and/or algaecide combined with an amplifying agent. The amplifying agent may comprise a polypeptide, such as a protein. The amplifying agent is added in an amount sufficient for the efficacy of the herbicide and/or algaecide to be improved. For instance, the presence of the amplifying agent allows for the herbicide and/or algaecide to be used at lower concentrations but have the same potency.

11 Claims, 2 Drawing Sheets

Figure 1. Mean (± 1 SE)

PLANT CONTROL COMPOSITION CONTAINING PEPTIDE ENHANCING AGENT

RELATED APPLICATIONS

The present application is based upon and claims priority to U.S. Provisional Patent Application having Ser. No. 61/865,679 filed on Aug. 14, 2013 and which is incorporated herein by reference.

FIELD OF THE INVENTION

The invention relates to a plant control composition containing a peptide enhancing agent.

BACKGROUND OF THE INVENTION

Many different pesticides, such as herbicides and algaecides, are commercially available for controlling unwanted plant and algae populations. The herbicides and algaecides are designed to limit growth and/or destroy a particular plant or algae or a broad range of plants and algae. The herbicide or algaecide may function in different ways. For instance, some herbicides and algaecides inhibit plant or algae growth by inhibiting photosynthesis. Other herbicides or algaecides are designed to be taken in by the plant or algae for inhibiting enzyme production. Other herbicides or algaecides may work as an oxidizer or may regulate plant growth by serving as an auxin mimic.

Of particular importance is that the herbicide or algaecide be capable of controlling growth or destroying a plant or algae population without harming the environment. For example, ideally a herbicide or algaecide will control plant or algae growth without having significant long-term adverse impacts on non-target organisms in the environment.

Particular problems are faced when attempting to control plant and algae growth in an aquatic environment, particularly in areas of high water exchange. Under these circumstances, the application of the herbicide or algaecide may not result in a high enough concentration to control the target organism. Given the use sites for aquatic herbicides and algaecides, a margin of safety for non-target organisms must be met, and therefore very small amounts of herbicides or algaecides are permitted for use in aquatic environments. These low concentrations, however, may not be sufficient to control a particular plant or algae population, given environmental conditions as those described above.

In view of the above, a need exists for a herbicide or algaecide enhancing agent that is capable of increasing the efficacy of a herbicide or algaecide without having to increase the amount of herbicide or algaecide applied to a given area.

SUMMARY OF THE INVENTION

In general, the present disclosure is directed to a plant or algae control composition that is capable of controlling a plant or algae population. Of particular advantage, the plant or algae control composition is efficacious at relatively low concentrations. The plant or algae control composition is particularly well-suited for treating water bodies, such as lakes, rivers, ponds, streams, creeks, tributaries, canals, and the like. In accordance with the present disclosure, the plant or algae control composition contains a first part comprising a herbicide and/or algaecide and a second part containing a herbicide or algaecide amplifying agent. The amplifying agent may comprise a peptide, such as a protein that may, in one embodiment, cause a plant or algae to increase its uptake of the herbicide or algaecide which, in turn, makes the herbicide or algaecide more potent even at low concentrations.

The first part and the second part of the plant or algae control composition can be blended and applied together. In still another embodiment, the second part of the composition may be first applied to a plant or algae population followed by the first part. In one particular embodiment, the present disclosure is directed to a plant or algae control composition that comprises a systemic herbicide or algaecide. The composition further contains a herbicide or algaecide amplifying agent. The herbicide or algaecide amplifying agent comprises a polypeptide and optionally a surfactant. For instance, in one embodiment, the herbicide or algaecide amplifying agent may comprise a polypeptide and surfactant complex.

The polypeptide present in the plant or algae control composition may be derived from natural sources or may be synthetically produced. In one embodiment, the polypeptide may comprise a protein that comprises an aerobic yeast fermentation supernatant. For instance, the polypeptide may be produced by yeast cells comprising *saccharomyces cerevisiae, kluyveromyces marxianus, kluyveromyces lactis, candida utilis, zygosaccharomyces, pichia, hansanula*, or mixtures thereof.

The herbicide or algaecide may be present in the composition in comparison to the herbicide or algaecide amplifying agent at a weight ratio from about 99:1 to about 50:50, such as from about 90:10 to about 70:30.

The present disclosure is also directed to a method of controlling a plant or algae population by contacting a plant or algae with the plant or algae control composition as described above. In one embodiment, the plant or algae is contacted with the plant or algae control composition by applying the composition to a body of water in which the plant or algae resides. When applied to a body of water, the herbicide or algaecide can be present in the water at a concentration of from about 0.001 ppm to about 50 ppm, while the polypeptide/surfactant blend can be present in the water at a concentration of about 0.3 ppm to about 15 ppm.

In other applications, the plant or algae control composition can be applied directly to a plant, such as to the leaves of a plant. In this embodiment, the plant control composition may be applied as a spray.

Other features and aspects of the present disclosure are discussed in greater detail below.

DETAILED DESCRIPTION

Figure 1:
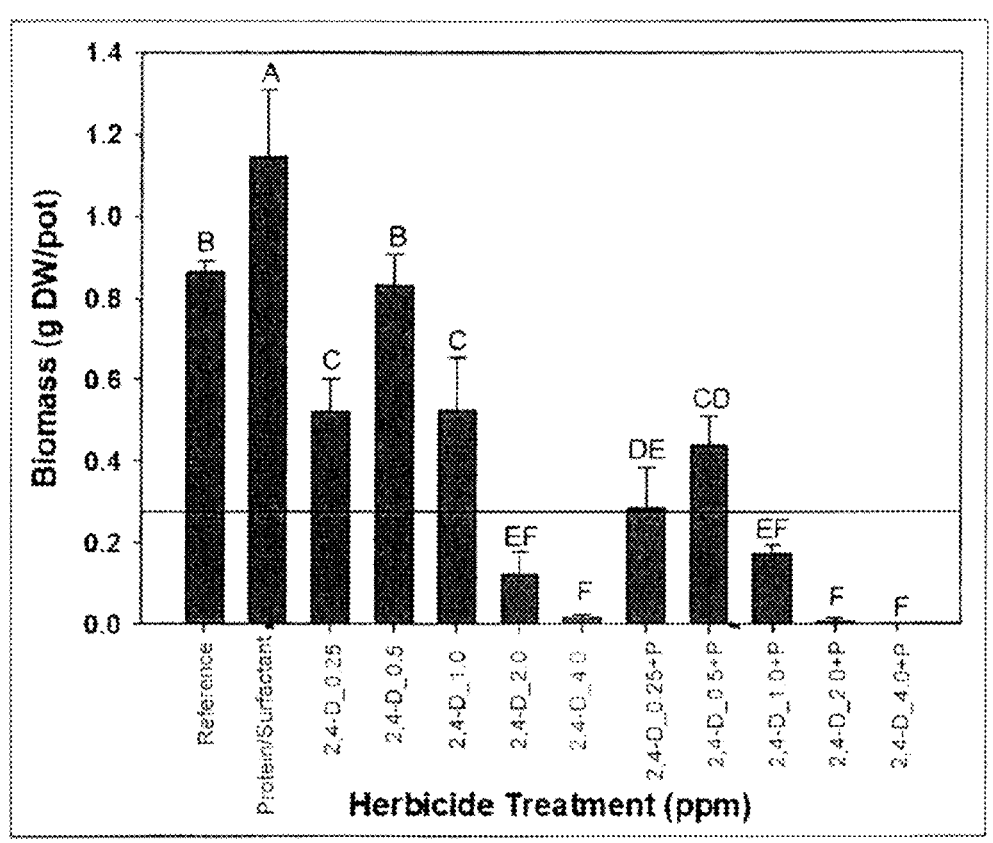
FIGS. 1 and 2 are graphical representations of the results obtained in Example 1 below.

It is to be understood by one of ordinary skill in the art that the present discussion is a description of exemplary embodiments only, and is not intended as limiting the broader aspects of the present disclosure.

In general, the present disclosure is directed to plant or algae control compositions for controlling a plant or algae population. The composition generally comprises a herbicide and/or algaecide combined with a herbicide or algaecide amplifying agent. In accordance with the present disclosure, the amplifying agent comprises a polypeptide, such as one or more proteins. The composition may further contain one or more surfactants. In one embodiment, for instance, the polypeptide and surfactant form a complex.

In the past, compositions of peptide and surface-agents have been used to increase catabolism. The compositions, for instance, were used for the treatment of municipal and industrial waste water treatment processes for the purposes of accelerating the biological degradation of organic containments. Such compositions are disclosed, for instance, in U.S. Pat. No. 7,476,529 and U.S. Pat. No. 8,323,949, which are both incorporated herein by reference.

According to the present disclosure, it was unexpectedly discovered that the presence of a polypeptide in conjunction with a herbicide or algaecide can enhance the activity of the herbicide or algaecide. In particular, the polypeptide has been found to synergistically associate with the herbicide or algaecide in a way that causes greater amounts of the herbicide or algaecide to be brought into the plant or algae, as indicated by increased efficacy on target organisms. Consequently, the presence of the polypeptide can decrease the amount or concentration of the herbicide or algaecide needed in order to have a lethal effect on the plant or algae population. The presence of the polypeptide can also shorten the response time of the herbicide or algaecide in controlling or destroying a plant or algae population. For instance, the concentration of the herbicide or algaecide may be reduced by greater than 20%, such as greater than 30%, such as greater than 40%, such as even greater than 50% when the herbicide or algaecide is used in conjunction with the polypeptide and have the same effect on the plant or algae composition when compared to using the herbicide or algaecide alone.

In general, any suitable herbicide or algaecide may be incorporated into the composition of the present disclosure. Herbicides and algaecides are generally categorized as systemic herbicides or algaecides or contact herbicides or algaecides. Systemic herbicides and algaecides have the capability to kill an entire plant and typically do so by being absorbed into the plant. Contact herbicides, on the other hand, cause parts of the plants to die that are in contact with the chemical. In the past, systemic herbicides have displayed a slower response time to kill a plant or algae and were typically used for seasonal control. When used in conjunction with a polypeptide according to the present disclosure, however, the response time of a systemic herbicide or algaecide can be greatly increased which may allow for the systemic herbicide or algaecide to be used in more and broader applications, such as in areas where herbicide contact time is limited.

One example of a herbicide or algaecide that may be present in the composition of the present disclosure is 2,4-D. 2,4-D comprises dichlorophenoxyacetic acid. 2,4-D has granular forms that can contain either 2,4-D dichlorophenoxy acetic acid, butoxyethyl ester, or the dimethylamine salt formulation of 2,4-D. 2,4-D can also be in liquid form that contains the dimethylamine salt of 2,4-D or 2,4-D in the acid form. 2,4-D is a systemic herbicide that also has selectivity. 2,4-D is known to control Eurasian watermilfoil and other broad-leaved plants. 2,4-D serves as an auxin mimic and thus regulates plant growth.

Another example of a herbicide or aquacide is bispyribac-sodium. Bispyribac-sodium comprises sodium 2,6-bis[(4,6-dimethoxypyrimidin-2-yl)oxy]benzoate. Bispyribac-sodium inhibits the production of enzymes for controlling plant growth. For instance, bispyribac-sodium is known as an ALS inhibitor, meaning that the chemical inhibits acetolactate synthase.

Another example of an enzyme inhibitor that may be incorporated in the composition of the present disclosure is carfentrazone-ethyl. Carfentrazone-ethyl inhibits PPO enzyme and the production of chlorophyll. Carfentrazone-ethyl generally comprises Ethyl 2-chloro-3-[2-chloro-4-fluoro-5-[4-(difluoromethyl)-4,5-dihydro-3-methyl-5-oxo-1H-1,2,4-trizol-1-yl]phenyl]propanoate.

Various different copper salts and copper complexes, both liquid and granular, may also be used as the herbicide or algaecide. When absorbed into a plant or algae, copper inhibits photosynthesis thus causing the plant or algae to die. Examples of copper compounds and copper complexes that may be used include copper sulfate pentahydrate, emulsified copper ethanolamine complexes, other copper ethanol copper complexes (including mixed copper ethanolamine complexes), chelates of copper gluconate and copper citrate; copper ethylenediamine complexes, and the like. Copper compounds and complexes are widely used as an algaecide. When used as an algaecide, however, problems have been experienced in dead biomass accumulating on the bottom of the water body. The accumulation of the dead biomass can, under some circumstances, create a hazard for fish through oxygen depletion as a result of large masses of decomposing algae in the water. When incorporated into the composition of the present disclosure, however, the copper compound and complex concentrations could be lowered which may alleviate some of these problems.

In still another embodiment, the herbicide or algaecide may comprise a diquat. Diquat generally comprises 6,7-Dihydrodipyrido[1,2-a:2',1'-c]pyrazinediium dibromide. Diquat inhibits photosynthesis and thus can rapidly control target plants and some algae. Diquat is a relatively fast-acting non-selective herbicide or algaecide which controls plant foliage that it comes in contact with, but typically does not translocate to the roots. Combining diquat with a polypeptide in accordance with the present disclosure can minimize the amount required while increasing its effectiveness.

Still another embodiment of a herbicide or algaecide that may be used in accordance with the present disclosure is endothall, which can comprise both a liquid and granular formulation. Endothall can comprise 3-dicarboxylic acid 7-oxabicyclo heptane-2. Endothall inhibits respiration and photosynthesis. Endothall is a non-selective herbicide or algaecide that works on contact and can work as a systemic pesticide. Endothall is typically used in very low concentration. Consequently, many benefits and advantages can be achieved if the efficacy of endothall can be improved while lowering its effective concentration.

Another herbicide or algaecide that may be used is flumioxazin. Flumioxazin comprises a N-phenyl phthalimide and, similar, to carfentrazone-ethyl, inhibits PPO enzyme and chlorophyll production.

Fluridone may also be used as the herbicide or algaecide. Fluridone is a systemic herbicide or algaecide that may be used to control various aquatic plants, including Eurasian watermilfoil and other underwater plants. Fluridone is available as a granular or as a liquid. Although fluridone can be selective and very useful against some plants and algaes, the chemical is very slow-acting. Combining fluridone with a polypeptide in accordance with the present disclosure, however, can dramatically increase response times.

Another herbicide or algaecide that may be used is glyphosate. Glyphosate is a plant enzyme inhibitor and comprises N-(phosphonomethyl)glycine. Glyphosate may be used as a systemic broad spectrum herbicide to control floating-leaved plants like water lilies and shoreline plants like Purple Loose Strife. In the past, several weeks were needed in order for glyphosate to effectively decrease a plant population. When combined with a polypeptide in accordance with the present disclosure, however, faster results may occur at lower concentrations.

In still another embodiment, the herbicide or algaecide may comprise imazamox. Imazamox comprises an ammonium salt of (2-[4,5-dihydro-4-methyl-4-(1-methylethyl)-5-oxo-1H-imidazol-2-yl]-5-(methoxymethyl)-3-pyridinecarboxylic acid. Imazamox is a plant enzyme inhibitor and inhibits ALS.

Another embodiment of a herbicide or algaecide is imazapyr, which is also a plant enzyme inhibitor. Imazapry can inhibit ALS enzymes. Imazapry comprises (RS)-2-(4-Methyl-5-oxo-4-propan-2-yl-1H-imidazol-2-yl)pyridine-3-carboxylic acid.

Another embodiment of a plant enzyme inhibitor is penoxsulam. Penoxsulam can also inhibit ALS enzyme. Chemically, penoxsulam may comprise 2-(2,2-difluoroethoxy)-6-trifluoromethyl-N-(5,8-dimethoxy[1,2,4]triazolo[1,5,-c]pyrimidin-2-yl))benzenesulfonamide).

In still another embodiment, the herbicide or algaecide may comprise triclopyr as either a liquid or granular formulation. Triclopyr generally comprises a triethylamine salt, and particularly, (3,5,6-trichloro-2-pyridinyloxyacetic acid). Triclopyr is an auxin mimic similar to that of the aforementioned 2,4-D and therefore is a plant growth regulator. Triclopyr is relatively fast-acting and can serve as a systemic, selective herbicide. Triclopyr will control populations of Eurasian watermilfoil and other broad-leaved species such Purple Loose Strife. Of particular advantage, triclopyr can control Eurasian watermilfoil, Purple Loose Strife, and other plants without affecting many grasses and sedges.

In still another embodiment, the herbicide or algaecide may comprise an oxidizer. Examples of oxidizers include various peroxides, particularly activated peroxides. Examples of oxidizers include sodium carbonate peroxyhydrate and hydrogen peroxide and peroxyacetic acid. Oxidizers can provide immediate control of algae. When controlling algae and other plants, the oxidizer may release oxygen. Thus, various advantages and benefits may be obtained if the concentration of the oxidizer may be decreased when combined with a polypeptide, thereby increasing the selectivity to target organisms.

As described above, in accordance with the present disclosure, a herbicide and/or algaecide is combined with an amplifying agent that comprises a polypeptide. The polypeptide may comprise a protein produced by an organism. Alternatively, the polypeptide may be synthetically produced. In one embodiment, a protein is incorporated into the composition that has a relatively low molecular weight. For instance, the molecular weight can be from about 5 kD to about 20 kD, such as about 8 kD to about 15 kD.

In one embodiment, the polypeptide incorporated into the composition comprises a protein produced by a microorganism, such as a yeast, during fermentation. Yeast strains that may be used to produce the polypeptide include *Saccharomyces cerevisiae, Kluyveromyces marxianus, Kluyveromyces lactis, Candida utilis* (*Torula* yeast), *Zygosaccharomyces, Pichia, Hansanula*, and mixtures thereof.

For instance, in one embodiment, one or more of the above yeast strains may be grown under aerobic conditions using a sugar. The yeast may be propagated under continuous aeration agitation at a temperature of from about 30° C. to about 38° C. and at a pH of from about 4.0 to about 6.5. Fermentation of the yeast occurs. After several hours to several days, the yeast fermentation product can be centrifuged to primarily isolate a protein produced by the yeast.

Optionally, the polypeptide may be associated with one or more surfactants. In a particular embodiment, the polypeptide may form a complex with a surfactant. The surfactant may comprise a non-ionic or an anionic surfactant. Alternatively, a blend of surfactants may be used including a non-ionic surfactant blended with an anionic surfactant.

Surfactants that are useful in the compositions described herein may be either non-ionic, anionic, amphoteric or cationic, or a combination of any of the above, depending on the application. Suitable non-ionic surfactants include alkanolamides, amine oxides, block polymers, ethoxylated primary and secondary alcohols, ethoxylated alkylphenols, ethoxylated fatty esters, sorbitan derivatives, glycerol esters, propoxylated and ethoxylated fatty acids, alcohols, and alkyl phenols, alkyl glucoside glycol esters, polymeric polysaccharides, sulfates and sulfonates of ethoxylated alkylphenols, and polymeric surfactants. Suitable anionic surfactants include ethoxylated amines and/or amides, sulfosuccinates and derivatives, sulfates of ethoxylated alcohols, sulfates of alcohols, sulfonates and sulfonic acid derivatives, phosphate esters, and polymeric surfactants. Suitable amphoteric surfactants include betaine derivatives. Suitable cationic surfactants include amine surfactants. Those skilled in the art will recognize that other and further surfactants are potentially useful in the compositions depending on the particular application. For example, a blend of non-ionic and anionic surfactants has been found to provide particularly good results.

Preferred anionic surfactants used in the composition include CalFoam™ ES 603, a sodium alcohol ether sulfate surfactant manufactured by Pilot Chemicals Co., and Steol™ CS 460, a sodium salt of an alkyl ether sulfate manufactured by Stepan Company. Preferred non-ionic surfactants used in the enzyme/surfactant compound include Neodol™ 25-7 or Neodol™ 25-9, which are C12-C15 linear primary alcohol ethoxylates manufactured by Shell Chemical Co., and Genapol™ 26 L-60, which is a C12-C16 natural linear alcohol ethoxylated to 60E C cloud point (approx. 7.3 mol), manufactured by Hoechst Celanese Corp. It should be understood that these surfactants and the surfactant classes described above are identified only as preferred materials and that this list is neither exclusive nor limiting of the composition.

The amount of herbicide and/or algaecide present in the composition and the amount of the polypeptide present in the composition can vary depending upon numerous factors. The relative amounts of the different components, for instance, can vary depending upon the type of plant or algae population being controlled and the desired result; and the environmental conditions present at the time of application. The relative amounts can also depend on the particular type of herbicide or algaecide present and the particular type of polypeptide present. In general, all herbicides and algaecides contained in the composition can be present in relation to the polypeptide at a weight ratio of from about 99:1 to about 50:50, such as from about 93:7 to about 80:20.

The composition of the present disclosure can be used to treat all different types of plants and algae. The composition, for instance, may be used to control plant populations on land. Alternatively, the composition may be added to a water body for treating aquatic plants and algae. The water body may comprise a fresh water system, such as lakes, streams, creeks, reservoirs, water canals, ponds, and the like.

When treating water bodies, the composition can be added to an aqueous system such that the concentration of the herbicide or algaecide in the water is from about 0.001 ppm to about 50 ppm while the concentration of the polypeptide/surfactant blend in the water can be from about 0.3 ppm to about 15 ppm. The herbicide and/or algaecide concentration exposure time can vary depending upon various factors including the type plant or algae being treated, the type of herbicide or algaecide present in the composition, and water exchange characteristics of the site.

In an alternative embodiment, the plant control composition of the present disclosure may be used as a spray. In this embodiment, the composition can be applied to water plants as well as land plants. The spray can be applied to the plants periodically until the desired result is achieved.

The composition of the present disclosure may be formulated in liquid form or in granular form depending upon the herbicide and/or algaecide used. In one embodiment, the composition may have two parts or components. The first component may contain the herbicide and/or algaecide. The second part or component, on the other hand, may contain the polypeptide and optionally a surfactant. In the two part system, the enhancing agent would applied first followed by the herbicide and/or algaecide at a later time. Alternatively, all of the ingredients may be combined together and applied to a plant or algae population simultaneously.

The present disclosure may be better understood with reference to the following examples.

EXAMPLES

Example 1

Five formulations were prepared and tested. The formulations included various pesticides used singularly, a protein surfactant blend used singularly, and pesticides used in combination with a protein surfactant blend. The tests were conducted on cyanophyta (blue-green algae) sampled from Morrison Lake located in Ionia County, Mich. The properties that were tested included the chlorophyll-a concentrations, cell densities, visual observations, and partial application label rates of chelated elemental copper and sodium carbonate peroxyhydrate. The initial chlorophyll-a concentration was determined to be 27.4 µg chlorophyll a/L. The initial water characteristics are listed in table 1.

TABLE 1

| Initial Water Characteristics in Morrison Lake | |
| --- | --- |
| pH (S.U.) | 8.5 |
| Dissolved Oxygen (mg $O_2$/L) | 9.25 |
| Alkalinity (mg $CaCO_3$/L) | 184 |
| Hardness (mg $CaCO_3$/L) | 230 |
| Conductivity (µS) | 471 |
| Temperature (° C.) | 24.1 |

Chelated Elemental Copper (10 Day Exposure)

The formulation tested was chelated elemental copper and the exposure period was 10 days. The growth chamber was maintained at 20±2° C., had photoperiods of 16 hours of light and 8 hours of dark, and had a light intensity of 3077 lux.

The algae were exposed to three concentrations in 500 mL flasks. The experiments were initiated using 300 mL of site water. The toxicity experiment was initiated by exposing the algae to 0.1, 0.2, 0.4, and 0.6 mg Cu as chelated elemental copper/L. Three replicates of each exposure concentration, along with three replicates of untreated controls, were tested. The results are shown in Table 2.

TABLE 2

Responses of algae in untreated controls and exposure concentrations of chelated elemental copper.

| Chelated Elemental Copper (mg Cu/L) | Day 10 Visual Observations | Avg. Day 4 Cell Density (cells/mL) | Avg. Day 4 Chlorophyll-a (µg/L) | Avg. Day 10 Cell Density (cells of/mL) | Avg. Day 10 Chlorophyll-a (µg/L) |
| --- | --- | --- | --- | --- | --- |
| Control | Algae on bottom, suspended & floating green | *Anabaena* sp. $2.42 \times 10^5$ *Aphanizomenon* sp. $1.1 \times 10^5$ | 29.6 | *Anabaena* sp. $2.03 \times 10^5$ *Aphanizomenon* sp. $9.6 \times 10^4$ | 23.7 |
| 0.1 (0.3 gallons/ acre-ft) | Algae on bottom & suspended, light green | *Anabaena* sp. $6.3 \times 10^4$ *Aphanizomenon* sp. $8.2 \times 10^3$ | 6.4 | *Anabaena* sp. $<1 \times 10^3$ *Aphanizomenon* sp. $3.1 \times 10^3$ | 2.9 |
| 0.2 (0.6 gallons/ acre-ft) | Algae on bottom white | *Anabaena* sp. $4.2 \times 10^4$ *Aphanizomenon* sp. $4.0 \times 10^3$ | <2 | Total algae $<1 \times 10^3$ | <2 |
| 0.4 (1.2 gallons/ acre-ft) | Algae on bottom white | *Anabaena* sp. $1.2 \times 10^4$ *Aphanizomenon* sp. $<1 \times 10^3$ | <2 | Total algae $<1 \times 10^3$ | <2 |
| 0.6 (1.8 gallons/ acre-ft) | Algae on bottom white | Total algae $<1 \times 10^3$ | <2 | Total algae $<1 \times 10^3$ | <2 |

Protein Surfactant Blend (4 Day Exposure)

The formulation tested was a protein surfactant blend and the exposure period was 4 days. The growth chamber was maintained at 20±2° C. had photoperiods of 16 hours of light and 8 hours of dark, and had a light intensity of 3077 lux.

The algae were exposed to three concentrations in 500 mL flasks. The experiments were initiated using 300 mL of site water. The toxicity experiment was initiated by exposing the algae to 0.5, 1.5, and 3.0 gallons of a protein surfactant blend/acre-ft. Three replicates of each exposure concentration, along with three replicates of untreated controls, were tested. The results are shown in Table 3.

TABLE 3

Responses of algae in untreated controls and exposure concentrations of a protein surfactant blend

| Protein Surfactant Blend (gallons/acre-ft) | Day 4 Visual Observations | Avg. Day 4 Cell Density (cells/mL) | Avg, Day 4 Chlorophyll-a (µg/L) |
|---|---|---|---|
| Control | Algae on bottom, suspended & floating green | *Anabaena* sp. $2.19 \times 10^5$ *Aphanizomenon* sp. $1.21 \times 10^5$ | 27.9 |
| 0.5 | Algae on bottom, suspended & floating green | *Anabaena* sp. $2.46 \times 10^3$ *Aphanizomenon* sp. $1.11 \times 10^5$ | 23.6 |
| 1.5 | Algae on bottom, suspended & floating green | *Anabaena* sp. $2.1 \times 10^5$ *Aphanizomenon* sp. $1.2 \times 10^5$ | 21.4 |
| 3.0 | Algae on bottom, suspended & floating green | *Anabaena* sp. $2.12 \times 10^5$ *Aphanizomenon* sp. $1.13 \times 10^3$ | 22.4 |

Sodium Carbonate Peroxyhydrate (10 Day Exposure)

The formulation tested was sodium carbonate peroxyhydrate and the exposure period was 10 days. The growth chamber was maintained at 20±2° C., had photoperiods of 16 hours of light and 8 hours of dark, and had a light intensity of 3077 lux.

The algae were exposed to three concentrations in 500 mL flasks. The experiments were initiated using 300 mL of site water. The toxicity experiment was initiated by exposing the algae to 7.4, 22.1, and 36.9 mg sodium carbonate peroxyhydrate/L. Three replicates of each exposure concentration, along with three replicates of untreated controls, were tested. The results are shown in Table 4.

TABLE 4

Responses of algae in untreated controls and exposure concentrations of sodium carbonate peroxyhydrate

| Sodium Carbonate Peroxyhydrate (mg/L) | Day 10 Visual Observations | Avg. Day 4 Cell Density (cells/mL) | Avg. Day 4 Chlorophyll-a (µg/L) | Avg. Day 10 Cell Density (cells of/mL) | Avg. Day 10 Chlorophyll-a (µg/L) |
|---|---|---|---|---|---|
| Control | Algae on bottom, suspended & floating green | *Anabaena* sp. $2.31 \times 10^5$ *Aphanizomenon* sp. $1.2 \times 10^5$ | 32.1 | *Anabaena* sp. $2.07 \times 10^5$ *Aphanizomenon* sp. $9.6 \times 10^4$ | 26.9 |
| 7.4 (20 lbs/acre-ft) | Algae on bottom & suspended, light green | *Anabaena* sp. $8.9 \times 10^4$ *Aphanizomenon* sp. $1.1 \times 10^3$ | 22.5 | *Anabaena* sp. $4.1 \times 10^4$ *Aphanizomenon* sp. $2.8 \times 10^4$ | 8.6 |
| 22.1 (60 lbs/acre-ft) | Algae on bottom white | *Anabaena* sp. $1.8 \times 10^4$ *Aphanizomenon* sp. $6.5 \times 10^4$ | 12.5 | Total algae $<1 \times 10^3$ | 2.7 |
| 36.9 (100 lbs/acre-ft) | Algae on bottom white | Total algae $<1 \times 10^3$ | 7.9 | Total algae $<1 \times 10^3$ | <2 |

Protein Surfactant Blend and Sodium Carbonate Peroxyhydrate (10 Day Exposure)

The formulation tested was sodium carbonate peroxyhydrate in combination with a protein surfactant blend and the exposure period was 10 days. The growth chamber was maintained at 20±2° C., had photoperiods of 16 hours of light and 8 hours of dark, and had a light intensity of 3077 lux.

The algae were exposed to three concentrations in 500 mL flasks. The experiments were initiated using 300 mL of site water. The toxicity experiment was initiated by exposing the algae to 0.5, 1.5, and 3.0 gallons of a protein surfactant blend/acre-ft followed by immediately adding 7.4, 22.1, and 36.9 mg sodium carbonate peroxyhydrate/L to the corresponding increasing treatments. Three replicates of each exposure, along with three replicates of untreated controls, were tested. The results are shown in table 5.

TABLE 5

Responses of algae in untreated controls and exposure concentrations of a protein surfactant blend followed immediately by sodium carbonate peroxyhydrate

| Protein Surfactant Blend (gallons/ acre-ft) | Sodium Carbonate Peroxyhydrate (mg/L) | Day 10 Visual Observations | Avg. Day 4 Cell Density (cells/mL) | Avg. Day 4 Chlorophyll-a ($\mu$g/L) | Avg. Day 10 Cell Density (cells of/mL) | Avg. Day 10 Chlorophyll-a ($\mu$g/L) |
|---|---|---|---|---|---|---|
| Control | Control | Algae on bottom, suspended & floating green | Anabaena sp. $2.42 \times 10^5$ Aphanizomenon sp. $1.1 \times 10^5$ | 28.5 | Anabaena sp. $2.22 \times 10^5$ Aphanizomenon sp. $1.28 \times 10^5$ | 28.7 |
| 0.5 | 7.4 (20 lbs/acre-ft) | Algae on bottom & suspended, light green | Anabaena sp. $7.5 \times 10^4$ Aphanizomenon sp. $1.21 \times 10^5$ | 22.1 | Anabaena sp. $2.3 \times 10^4$ Aphanizomenon sp. $1.16 \times 10^4$ | 8.8 |
| 1.5 | 22.1 (60 lbs/acre-ft) | Algae on bottom & suspended, light green | Anabaena sp. $7.1 \times 10^3$ Aphanizomenon sp. $4.0 \times 10^4$ | 16.9 | Anabaena sp. $3.9 \times 10^3$ Aphanizomenon sp. $1.6 \times 10^3$ | 7.6 |
| 3.0 | 36.9 (100 lbs/acre-ft) | Algae on bottom white | Total algae $<1 \times 10^3$ | 3.7 | Total algae $<1 \times 10^3$ | 5.5 |

Protein Surfactant Blend and Sodium Carbonate Peroxyhydrate (4 Day=>6 Day Exposure)

The formulation tested was a protein surfactant blend and the exposure period was four days. After four days, sodium carbonate peroxyhydrate was added and the combination had an exposure time of six days. The growth chamber was maintained at 20±2° C., had photoperiods of 16 hours of light and 8 hours of dark, and had a light intensity of 3077 lux.

The algae were exposed to three concentrations in 500 mL flasks. The experiments were initiated using 300 mL of site water. The toxicity experiment was initiated by exposing the algae to 0.5, 1.5, and 3.0 gallons of a protein surfactant blend/acre-ft followed after four days by adding 7.4, 22.1, and 36.9 mg sodium carbonate peroxyhydrate/L to the corresponding increasing treatments. Three replicates of each exposure, along with three replicates of untreated controls, were tested. The results are in table 6.

TABLE 6

Responses of algae in untreated controls and exposure concentrations of a protein surfactant blend followed after four days by sodium carbonate peroxyhydrate

| Protein Surfactant Blend (gallons/ acre-ft) | Sodium Carbonate Peroxyhydrate (mg/L) | Day 10 Visual Observations | Avg. Day 4 Cell Density (cells/mL) | Avg. Day 4 Chlorophyll-a ($\mu$g/L) | Avg. Day 10 Cell Density (cells of/mL) | Avg. Day 10 Chlorophyll-a ($\mu$g/L) |
|---|---|---|---|---|---|---|
| Control | Control | Algae on bottom, suspended & floating green | Anabaena sp. $2.19 \times 10^5$ Aphanizomenon sp. $1.21 \times 10^5$ | 27.9 | Anabaena sp. $2.31 \times 10^5$ Aphanizomenon sp. $9.11 \times 10^4$ | 25.2 |

TABLE 6-continued

Responses of algae in untreated controls and exposure concentrations of a protein surfactant blend followed after four days by sodium carbonate peroxyhydrate

| Protein Surfactant Blend (gallons/acre-ft) | Sodium Carbonate Peroxyhydrate (mg/L) | Day 10 Visual Observations | Avg. Day 4 Cell Density (cells/mL) | Avg. Day 4 Chlorophyll-a (µg/L) | Avg. Day 10 Cell Density (cells of/mL) | Avg. Day 10 Chlorophyll-a (µg/L) |
|---|---|---|---|---|---|---|
| 0.5 | 7.4 (20 lbs/acre-ft) | Algae on bottom & suspended, light green | *Anabaena* sp. $2.46 \times 10^5$ *Aphanizomenon* sp. $1.11 \times 10^5$ | 23.6 | Total algae $1 \times 10^3$ | 3.9 |
| 1.5 | 22.1 (60 lbs/acre-ft) | Algae on bottom white | *Anabaena* sp. $2.1 \times 10^5$ *Aphanizomenon* sp. $1.2 \times 10^5$ | 21.4 | Total algae $1 \times 10^3$ | 2.3 |
| 3.0 | 36.9 (100 lbs/acre-ft) | Algae on bottom white | *Anabaena* sp. $2.12 \times 10^5$ *Aphanizomenon* sp. $1.13 \times 10^5$ | 22.4 | Total algae $<1 \times 10^3$ | <2 |

The concentration of sodium carbonate peroxyhydrate needed for algae control was three fold less (7.4 ppm) when applied 4 days after the protein surfactant blend than when sodium carbonate peroxyhydrate was applied alone at 22.7 ppm.

Example 2

Eurasian watermilfoil was tested in this example. Two apical tips approximately 15 cm long were planted into each of 96, 16 ounce plastic pots. The pots were filled with Black Kow potting soil and amended with 2 g/L Osmocote fertilizer (19-6-12). Six pots of potted Eurasian watermilfoil were placed into each of 16 aquaria. Aquaria were filled to a volume of 45 L and plants allowed to grow approximately 2-3 weeks prior to herbicide treatments. Pre-treatment biomass was harvested by collecting above ground biomass of plants in one pot per aquaria. Plant material were dried and weighed to assess biomass.

After pre-treatment data collection, liquid 2,4-D acid was applied alone and in combination with the protein surfactant blend of Example 1 at the rates outlined in Table 1. The contact herbicide carfentrazone-ethyl was evaluated alone and in combination with the protein surfactant blend as well. An untreated reference was included for comparison purposes. All herbicide applications were made using an 8 hr exposure. A short exposure time was used to ensure that any enhanced efficacy that was observed could be attributed to the protein surfactant blend as threshold levels of control for Eurasian watermilfoil with 2,4-D alone are typically 1 mg ae/L for 48 hrs, and 2 mg ae/L for 36 or 48 hrs of exposure. After the 8 hr exposure time was reached, each aquaria was drained and refilled with fresh water to remove any herbicide residues remaining in the water column.

TABLE 1

Treatment rates for the Eurasian watermilfoil trial.

| Treatment Number | Protein Surfactant Blend* (application rate of 0.5 gal/acre-ft.) mL/aquaria | 2,4-D Concentration (ppm) | Carfentrazone-etheyl (ppm) |
|---|---|---|---|
| 1 | 0 | 0 | 0 |
| 2 | 0.072 | 0 | 0 |
| 3 | 0 | 0.25 | 0 |
| 4 | 0 | 0.5 | 0 |
| 5 | 0 | 1.0 | 0 |
| 6 | 0 | 2.0 | 0 |
| 7 | 0 | 4.0 | 0 |
| 8 | 0.072 | 0.25 | 0 |
| 9 | 0.072 | 0.5 | 0 |
| 10 | 0.072 | 1.0 | 0 |
| 11 | 0.072 | 2.0 | 0 |
| 12 | 0.072 | 4.0 | 0 |
| 13 | 0 | 0 | 0.1 |
| 14 | 0 | 0 | 0.2 |
| 15 | 0.072 | 0 | 0.1 |
| 16 | 0.072 | 6 | 0.2 |

Four weeks after treatment (WAT), living biomass was dried and weighed for biomass determination. Differences between treatments were analyzed using ANOVA with means separated using a Fisher's Protected LSD test. Exponential decay regression models were developed to determine $LC_{50}$ values for Eurasian watermilfoil treated with 2,4-D alone and with 2,4-D+ the protein surfactant blend across a range of 2,4-D concentrations. All analyses were conducted at a $p \leq 0.05$ significance level. At the time of treatment Eurasian watermilfoil growth in all aquaria was similar (p=0.31) as indicated by pre treatment plant heights.

Figure 2:
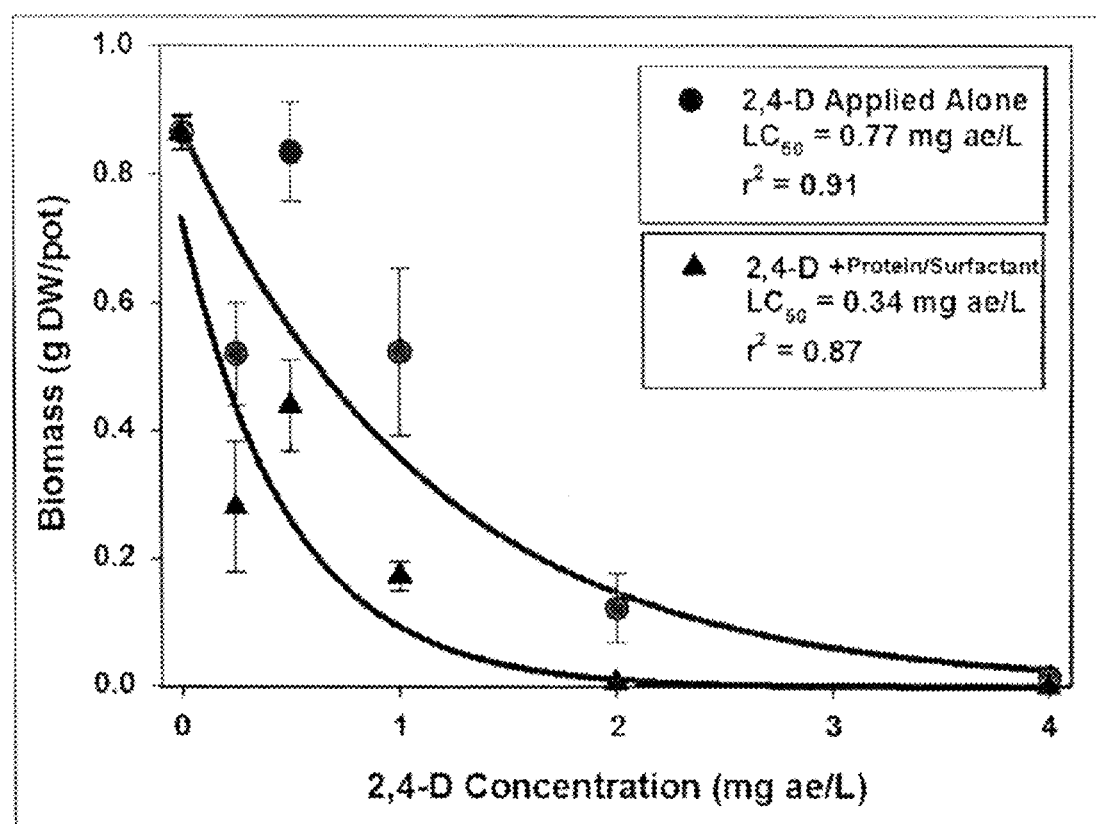

The results are shown in FIG. 1 and FIG. 2. Plant biomass in the untreated reference aquaria was 67% higher 4 WAT than pre treatment levels (FIG. 1).

FIG. 1 illustrates Eurasian watermilfoil biomass following applications of 2,4-D alone and in combination with the protein surfactant compound using an 8 hour exposure time. The protein surfactant compound was applied at 0.072 mL/aquaria which corresponds to a rate of 0.5 gallons/acre ft. In the figure, bars sharing the same letter are not significantly different according to a Fisher's Protected LSD test at a p≤0.05 significant level.

FIG. 2 illustrates Eurasian watermilfoil biomass response curves based on increasing 2,4-D concentrations. The green line (corresponding to circles) is Eurasian watermilfoil response when 2,4-D was applied alone, and the blue line (corresponding to triangles) is Eurasian watermilfoil response when 2,4-D was applied in combination with the protein surfactant compound using an 8 hr exposure.

Carfentrazone-ethyl was only effective at reducing Eurasian watermilfoil biomass using the 0.2 mg ai/L concentration at 4 WAT. There was initial injury observed using the 0.1 mg ai/L concentration of carfentrazone-ethyl, however regrowth was noted at 2 WAT.

The use of 2,4-D resulted in biomass reductions for all concentrations and combinations with the exception of 2,4-D applied alone at 0.5 mg ae/L when compared to untreated reference plants (FIG. 1). However, when the protein surfactant blend was used in combination with 2,4-D it provided greater Eurasian watermilfoil control at every concentration than the same 2,4-D concentration applied alone with the exception of the 0.5 mg ae/L+ protein surfactant blend treatment (see FIG. 1 and FIG. 2). Based on this data, the combination of 2,4-D at 1.0 mg ae/L and the protein surfactant blend provided dramatic improvements. This combination offered greater control than the same 2,4-D concentration applied alone, and similar Eurasian watermilfoil control as 2,4-D applied at 2.0 and 4.0 mg ae/L alone. Based on previous concentration exposure time studies, 2,4-D applied alone at concentrations of 2.0 mg ae/L or above typically need 12 hrs exposure to be efficacious against Eurasian watermilfoil. Under the current experimental design, biomass reductions were achieved with an 8 hr exposure.

The addition of the protein surfactant blend stimulated Eurasian watermilfoil growth and thereby increased the rate at which 2,4-D was taken up by individual plants resulting in the delivery of a lethal dose faster than 2,4-D applied alone. Pursuant to this, not only was the rate of 2,4-D uptake likely affected with the addition of the protein surfactant blend, but the amount of 2,4-D taken into the plant may have also been increased. In other words, greater efficacy can be attained at reduced 2,4-D concentrations in the presence of the protein surfactant blend than when the protein surfactant blend is not applied.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A method of controlling growth of an aquatic plant or algae population wherein the plant or algae is contained in a body of water, comprising contacting the aquatic plant or algae with a plant control composition by adding the plant control composition to a body of water, the plant control composition comprising:
   an aquatic herbicide or algaecide; and
   a herbicide or algaecide amplifying agent, the herbicide or algaecide amplifying agent comprising a polypeptide and a surfactant, the polypeptide and surfactant comprising a polypeptide and surfactant complex, and wherein the polypeptide is present in an amount sufficient to increase a kill rate and shorten a response time of the aquatic herbicide or algaecide when contacted with a plant or algae; and
   wherein the aquatic herbicide or algaecide comprises dichiorophenoxyacetic acid or derivative thereof, bispyribac-sodium, carfentrazone-ethyl, a copper salt, a copper complex, a diquat, endothall, flumioxazin, fluridone, imazamox, imazapyr, penoxsulam, triclopyr, sodium carbonate peroxyhydrate, hydrogen peroxide and peroxyacetic acid, or mixtures thereof.

2. A method of controlling growth of an aquatic plant or algae population as defined in claim 1, wherein the concentration of the aquatic herbicide or algaecide is reduced by greater than 20% when the aquatic herbicide or algaecide is used in combination with the polypeptide and have the same effect on a plant or algae population when compared to using the aquatic herbicide or algaecide alone.

3. A method of controlling growth of an aquatic plant or algae population as defined in claim 1, wherein the aquatic herbicide or algaecide and the polypeptide are present in the composition at a weight ratio of from about 99:1 to about 50:50.

4. A method of controlling growth of an aquatic plant or algae population as defined in claim 1, wherein the aquatic herbicide or algaecide and the polypeptide are present in the composition at a weight ratio of from about 93:7 to about 80:20.

5. A method of controlling growth of an aquatic plant or algae population as defined in claim 1 wherein the aquatic herbicide or algaecide is used to control aquatic broad-leaved species, underwater plants, floating-leaved plants, shoreline plants, or algae.

6. A method of controlling growth of an aquatic plant or algae population as defined in claim 5 wherein the aquatic herbicide or algaecide is used to control watermilfoil.

7. A method of controlling growth of an aquatic plant or algae population as defined in claim 5 wherein the aquatic herbicide or algaecide is used to control cyanophyta.

8. A method of controlling growth of an aquatic plant or algae population as defined in claim 1, wherein the plant control composition is added to the body of water such that the herbicide or algaecide is present in the water in an amount from about 0.001 ppm to about 50 ppm and the polypeptide is present in the water in an amount from about 0.3 ppm to about 15 ppm.

9. A method of controlling growth of an aquatic plant or algae population comprising contacting the aquatic plant or algae with a two part plant control system by adding the two part plant control system to a body of water, the two part plant control composition comprising:
   a first part comprising a herbicide or algaecide amplifying agent, the herbicide or algaecide amplifying agent comprising a polypeptide and a surfactant, the polypeptide and surfactant comprising a polypeptide and surfactant complex, and wherein the polypeptide is present in an amount sufficient to increase a kill rate of the herbicide or algaecide when contacted with a plant or algae; and
   a second part comprising a herbicide or algaecide,
   wherein the first part and the second part of the plant control system are blended together prior to adding to the body of water or are applied individually to the body of water; and
   wherein the herbicide or algaecide comprises dichlorophenoxyacetic acid or derivative thereof, bispyribac-sodium, carfentrazone-ethyl, a copper salt, a copper complex, a diquat, endothall, flumioxazin, fluridone, imazamox, imazapyr, penoxsulam, triclopyr, sodium carbonate peroxyhydrate, hydrogen peroxide and peroxyacetic acid, or mixtures thereof.

10. A method of controlling growth of an aquatic plant or algae population as defined in claim 9, wherein both the first part of the plant control system and the second part of the plant control system are applied simultaneously.

11. A method of controlling growth of an aquatic plant or algae population as defined in claim 9, wherein the second part of the plant control system is applied and then the first part of the plant control system is applied.

* * * * *